(12) United States Patent (10) Patent No.: US 8,831,899 B2
Nemoto et al. (45) Date of Patent: Sep. 9, 2014

(54) INSPECTING APPARATUS AND AN INSPECTING METHOD

(75) Inventors: Kazunori Nemoto, Akishima (JP); Akira Hamamatsu, Chiba (JP); Hideo Ota, Yokohama (JP); Kenji Oka, Hitachinaka (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 457 days.

(21) Appl. No.: 13/127,051

(22) PCT Filed: Oct. 15, 2009

(86) PCT No.: PCT/JP2009/067837
§ 371 (c)(1),
(2), (4) Date: Jul. 25, 2011

(87) PCT Pub. No.: WO2010/050365
PCT Pub. Date: May 6, 2010

(65) Prior Publication Data
US 2011/0276299 A1 Nov. 10, 2011

(30) Foreign Application Priority Data
Oct. 31, 2008 (JP) .................................. 2008-281498

(51) Int. Cl.
*G01C 19/00* (2013.01)
(Continued)

(52) U.S. Cl.
CPC .............. *G01B 11/303* (2013.01); *B82Y 35/00* (2013.01); *G01N 21/93* (2013.01); *G01N 2021/8822* (2013.01); *G01N 21/9501* (2013.01); *H01L 22/12* (2013.01)
USPC ........................................ 702/104; 356/237.5

(58) Field of Classification Search
USPC ............... 702/104, 81, 84–85, 106, 117, 121, 702/127, 172, 182, 189, 198–199; 356/51, 356/73, 237.2, 237.4–237.5, 337, 341, 445, 356/448, 600–601, 625, 629; 250/234, 250/492.1–492.2; 700/95, 108–110, 117, 700/121; 73/1.01, 1.89, 105
See application file for complete search history.

(56) References Cited

U.S. PATENT DOCUMENTS 5,533,387 A 7/1996 Aihara et al.
5,955,654 A * 9/1999 Stover et al. .................... 73/1.89

(Continued)

FOREIGN PATENT DOCUMENTS

JP 08-088257 A 4/1996
JP 10-172940 A 6/1998

(Continued)

OTHER PUBLICATIONS

Deumie et al., Multiscale Roughness in Optical Multilayers: Atomic Force Microscopy and Light Scattering, Oct. 1, 1996, Applied Optics, vol. 35, No. 28, pp. 5583-5594.*

(Continued)

*Primary Examiner* — Toan Le
(74) *Attorney, Agent, or Firm* — Miles & Stockbridge P.C.

(57) ABSTRACT

A system and method for determining measurement results of a dark-field inspection apparatus up to a microscopic area. A dark-field inspection apparatus is calibrated using a reference wafer having microroughness of an irregular asperity pattern accurately formed on a surface, and the microroughness of the surface having an ensured microroughness degree. This microroughness is measured by using an AFM, and an expected haze value is obtained based on the measured value. Then, haze of the surface of the reference wafer is measured by the dark-field inspection apparatus to be inspected to obtain an actually-measured haze value, and a difference between the expected haze value and the actually-measured haze value is obtained. Based on this difference, a haze measurement parameter of the dark-field inspection apparatus is adjusted so that the actually-measured haze value and the expected haze value match each other.

30 Claims, 14 Drawing Sheets

(51) Int. Cl.
- G01N 21/00 (2006.01)
- B82Y 35/00 (2011.01)
- G01N 21/93 (2006.01)
- G01B 11/30 (2006.01)
- G01N 21/95 (2006.01)
- G01N 21/88 (2006.01)
- H01L 21/66 (2006.01)

(56) References Cited

U.S. PATENT DOCUMENTS

| | | | |
|---|---|---|---|
| 6,016,684 A | 1/2000 | Scheer et al. | |
| 6,463,941 B1 * | 10/2002 | Takita | 134/57 R |
| 6,552,337 B1 | 4/2003 | Cho et al. | |
| 6,830,943 B1 | 12/2004 | Lo et al. | |
| 2006/0197945 A1 * | 9/2006 | Tiemeyer et al. | 356/237.2 |

FOREIGN PATENT DOCUMENTS

| | | |
|---|---|---|
| JP | 2000-031224 A | 1/2000 |
| JP | 2000-183017 A | 6/2000 |
| JP | 2001-201448 A | 7/2001 |
| JP | 2001-338959 A | 12/2001 |
| JP | 2002-134581 A | 5/2002 |
| JP | 2003-240723 A | 8/2003 |
| JP | 2006-278515 A | 10/2006 |
| JP | 2006-278972 A | 10/2006 |
| WO | WO 99/46558 A1 | 9/1999 |

OTHER PUBLICATIONS

Amra et al., Overlapping of Roughness Spectra Measured in Macroscopic (Optical) and Microscopic (AFM) Bandwidths, 1994, SPIE, vol. 2253, pp. 614-630.*

Duparre et al., Surface Characterization Techniques for Determining the Root-Mean-Square Roughness and Power Spectral Densities of Optical Components, Jan. 1, 2002, Applied Optics, vol. 41, No. 1, pp. 154-171.*

B.W. Scheer, Development of a Physical Haze and Microroughness Standard, 1996, SPIE, vol. 2862, pp. 78-95.*

Office Action issued Mar. 26, 2013, in Japanese Patent Application No. 2008-281498.

* cited by examiner

| MEASURED WAFER | DETECTED VOLTAGE VALUE | EXPECTED HAZE VALUE | ACTUALLY-MEASURED HAZE VALUE |
|---|---|---|---|
| SLOT 1 | 90 | 100 | 1.60 |
| SLOT 2 | 190 | 200 | 1.80 |
| SLOT 3 | 285 | 300 | 2.00 |

| MEASURED REGION | DETECTED VOLTAGE VALUE | EXPECTED HAZE VALUE | ACTUALLY-MEASURED HAZE VALUE |
|---|---|---|---|
| 24A | 90 | 100 | 1.60 |
| 24B | 190 | 200 | 1.80 |
| 24C | 285 | 300 | 2.00 |

INSPECTING APPARATUS AND AN INSPECTING METHOD

TECHNICAL FIELD

The present invention relates to a reference wafer for calibration of dark-field inspection apparatuses, a method of manufacturing a reference wafer for calibration of dark-field inspection apparatuses, a method of calibrating a dark-field inspection apparatus, a dark-field inspection apparatus, and a wafer inspection technology.

BACKGROUND ART

Japanese Patent Application Laid-Open Publication No. 2002-134581 (Patent Document 1) mentions a reference wafer as a reference when microscopic asperities on the surface of a silicon wafer are measured, and discloses a technology of forming microscopic asperities on the surface by relative scanning of local etching when the reference wafer is manufactured. The document also discloses that $NF_3$, $CF_4$, or $SF_6$, which is an active-species gas, is used in the local etching.

Japanese Patent Application Laid-Open Publication No. 2000-183017 (Patent Document 2 and corresponding U.S. Pat. No. 6,463,941) discloses a chemical-solution concentration control apparatus that controls the concentration of a chemical solution for use in wafer etching and cleaning and others, and discloses a mixed solution of ammonia and a hydrogen peroxide solution as an example of the chemical solution.

Japanese Patent Application Laid-Open Publication No. 10-172940 (Patent Document 3) discloses a silicon wafer cleaning apparatus that makes an adjustment so that the concentration of a chemical solution for use in silicon wafer cleaning is optimum, and discloses a mixed solution of ammonia and a hydrogen peroxide solution as an example of the chemical solution.

U.S. Pat. No. 6,830,943 (Patent Document 4) discloses a wafer including a calibration standard for semiconductor metrology, in which the wafer has a surface with a degree of roughness less than 1 Å and has a calibration layer formed of a metal oxide or the like on the surface of the wafer.

PRIOR ART DOCUMENTS

Patent Document

Patent Document 1: Japanese Patent Application Laid-Open Publication No. 2002-134581
Patent Document 2: Japanese Patent Application Laid-Open Publication No. 2000-183017
Patent Document 3: Japanese Patent Application Laid-Open Publication No. 10-172940
Patent Document 4: U.S. Pat. No. 6,830,943

DISCLOSURE OF THE INVENTION

Problem to be Solved by the Invention

A single crystal silicon wafer (hereinafter simply referred to as a wafer) as a material of a substrate of a semiconductor device is created as a mirror wafer by slicing a single crystal silicon ingot pulled by Czochralski method (CZ method) or the like, through wire-saw cutting or the like, and then, through grinding, etching, surface mirror polishing, wet cleaning, and others.

In recent years, with semiconductor devices being miniaturized and their performance being increased, enhancement of the quality of the surface of a wafer as a material of a substrate has been demanded. Here, indexes to the surface quality of a wafer include a crystal defect, flatness, nanotopography, particles, metal impurities, organic substances, microroughness, natural oxide films, and others.

In a semiconductor device, even a slight change in microroughness on the surface of the wafer may invite deterioration in characteristics. Therefore, the inventors of the present invention have studied a technology of measuring microroughness among the indexes to the surface quality of the wafer mentioned above by using a dark-field inspection apparatus. In measurement of microroughness by the dark-field inspection apparatus, a mirror wafer is illuminated, and haze is optically measured. Haze refers to a surface state of a wafer when a mirror wafer is irradiated with light, in which light is scattered in directions around the whole circumference due to roughness (asperities) of a surface of the wafer. By receiving scattered light, an average value of roughness degrees of haze can be calculated. The inventors have obtained the following problems in calibrating a haze measuring function of the dark-field inspection apparatus.

More specifically, in calibrating the haze measuring function of the dark-field inspection apparatus with high accuracy, the surface of a wafer for reference for use in calibration is required to have submicroscopic microroughness on the order of, for example, 0.1 nm to 0.2 nm, which is a most microscopic roughness degree for a thin film for use in semiconductor device manufacturing, reproduced thereon. Therefore, a problem is to form such submicroscopic microroughness on the surface of the wafer for reference with high accuracy.

A preferred aim of the present invention is to provide a technology capable of producing a reference wafer for calibration having submicroscopic roughness on its surface.

Another preferred aim of the present invention is to provide a technology capable of reducing a difference in measurement capability among dark-field inspection apparatuses of the same type.

Still another preferred aim of the present invention is to provide a technology capable of ensuring the measurement results of a dark-field inspection apparatus up to a microscopic area.

Yet another preferred aim of the present invention is to provide a technology of detecting and adjusting changes with time in measurement capability of a dark-field inspection apparatus.

The above and other preferred aims and novel characteristics of the present invention will be apparent from the description of the present specification and the accompanying drawings.

Means for Solving the Problems

The typical ones of the inventions disclosed in the present application will be briefly described as follows.

(1) In the present invention, microroughness is controlled by using a chemical solution.

(2) In the present invention, a dark-field inspection apparatus is calibrated by using a wafer with microroughness controlled by using a chemical solution (hereinafter, referred to as a reference wafer for calibration of dark-field inspection apparatuses).

(3) In the present invention, a scanning-type probe microscope is used to calibrate a dark-field inspection apparatus using a reference wafer for calibration of dark-field inspection apparatuses.

(4) In the present invention, a wafer is inspected by using a dark-field inspection apparatus calibrated by using a reference wafer for calibration of dark-field inspection apparatuses.

(5) In a reference wafer for calibration of dark-field inspection apparatuses according to the present invention, the reference wafer is formed of a bulk wafer without a thin film formed on a surface, haze due to microroughness of an irregular pattern is formed on the surface, the microroughness is formed in a chemical reaction using a chemical solution, and a dark-field inspection apparatus is calibrated by measuring the haze.

(6) A method of manufacturing a reference wafer for calibration of dark-field inspection apparatuses according to the present invention includes the steps of: (a) providing a bulk wafer without a thin film formed on a surface; and (b) causing a chemical reaction between the surface of the bulk wafer and a chemical solution for forming microroughness of an irregular pattern on the surface of the bulk wafer, in which the microroughness forms haze, and a dark-field inspection apparatus is calibrated by measuring the haze.

(7) A calibration method of a dark-field inspection apparatus according to the present invention includes the steps of: (a) providing a reference wafer for calibration of dark-field inspection apparatuses having haze formed on a surface; (b) measuring a roughness degree of microroughness of the surface of the reference wafer for dark-field inspection apparatuses having the haze formed thereon with a microscope capable of measuring asperities at an atomic level for imaging, performing a simulation of measurement of the haze with a dark-field inspection apparatus based on the measured roughness degree, and obtaining an expected haze value by the simulation; (c) actually measuring the haze with the dark-field inspection apparatus and obtaining an actually-measured haze value by actual measurement; (d) analyzing a difference between the expected haze value and the actually-measured haze value; and (e) calibrating the dark-field inspection apparatus based on the difference, in which the reference wafer for dark-field inspection apparatuses is formed of a bulk wafer without a thin film formed on a surface, the haze is formed according to the microroughness of an irregular pattern, and the microroughness is formed in a chemical reaction using a chemical solution.

(8) A dark-field inspection apparatus according to the present invention that inspects the presence or absence of a foreign substance or a roughness degree of a surface of a first bulk wafer without a pattern of a thin film, a device, or a wiring formed on the surface, the dark-field inspection apparatus being calibrated by the steps of: (a) providing a reference wafer for calibration of dark-field inspection apparatuses having haze formed on a surface; (b) measuring a roughness degree of microroughness of the surface of the reference wafer for dark-field inspection apparatuses having the haze formed thereon with a microscope capable of measuring asperities at an atomic level for imaging, performing a simulation of measurement of the haze with a dark-field inspection apparatus based on the measured roughness degree, and obtaining an expected haze value by the simulation; (c) actually measuring the haze with the dark-field inspection apparatus and obtaining an actually-measured haze value by actual measurement; (d) analyzing a difference between the expected haze value and the actually-measured haze value; and (e) calibrating the dark-field inspection apparatus based on the difference, in which the reference wafer for dark-field inspection apparatuses is formed of a second bulk wafer without a thin film formed on a surface, the haze is formed according to the microroughness of an irregular pattern, and the microroughness is formed in a chemical reaction using a chemical solution.

(9) A wafer inspecting method according to the present invention, the method inspecting, by using a dark-field inspection apparatus, a first bulk wafer to be inspected without a pattern of a thin film, a device, or a wiring formed on a surface, in which the dark-field inspection apparatus is calibrated by the steps of: (a) providing a reference wafer for calibration of dark-field inspection apparatuses having haze formed on a surface; (b) measuring a roughness degree of microroughness of the surface of the reference wafer for dark-field inspection apparatuses having the haze formed thereon with a microscope capable of measuring asperities at anatomic level for imaging, performing a simulation of measurement of the haze with the dark-field inspection apparatus based on the measured roughness degree, and obtaining an expected haze value by the simulation; (c) actually measuring the haze with the dark-field inspection apparatus and obtaining an actually-measured haze value by actual measurement; (d) analyzing a difference between the expected haze value and the actually-measured haze value; and (e) calibrating the dark-field inspection apparatus based on the difference, the reference wafer for dark-field inspection apparatuses is formed of a second bulk wafer without a thin film formed on a surface, the haze is formed due to the microroughness of an irregular pattern, and the microroughness is formed in a chemical reaction using a chemical solution.

Effects of the Invention

The effects obtained by typical aspects of the present invention will be briefly described below.

(1) A reference wafer for calibration having submicroscopic microroughness on its surface can be produced.

(2) A difference in measurement capability among dark-field inspection apparatuses of the same type can be reduced.

(3) The measurement capability of a dark-field inspection apparatus can be ensured up to a microscopic area.

(4) Changes with time in measurement capability of a dark-field inspection apparatus can be detected and adjusted.

BRIEF DESCRIPTIONS OF DRAWINGS

Figure 16:
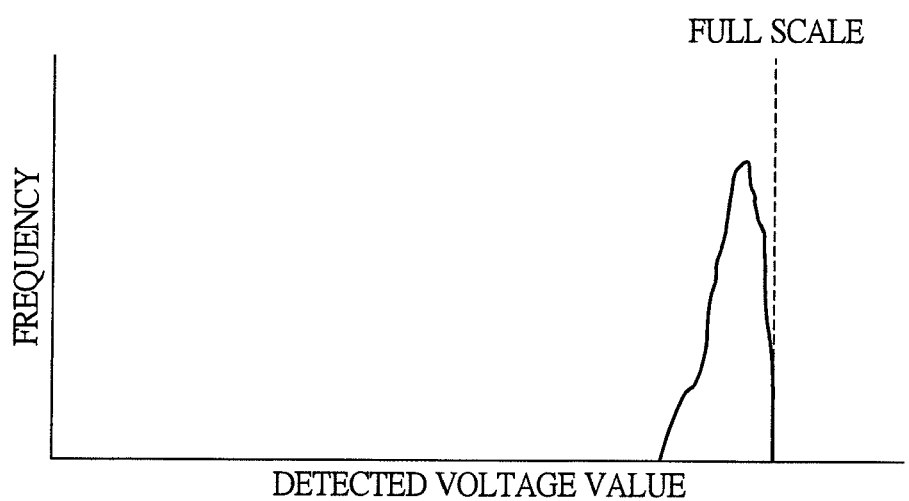
Figure 17:
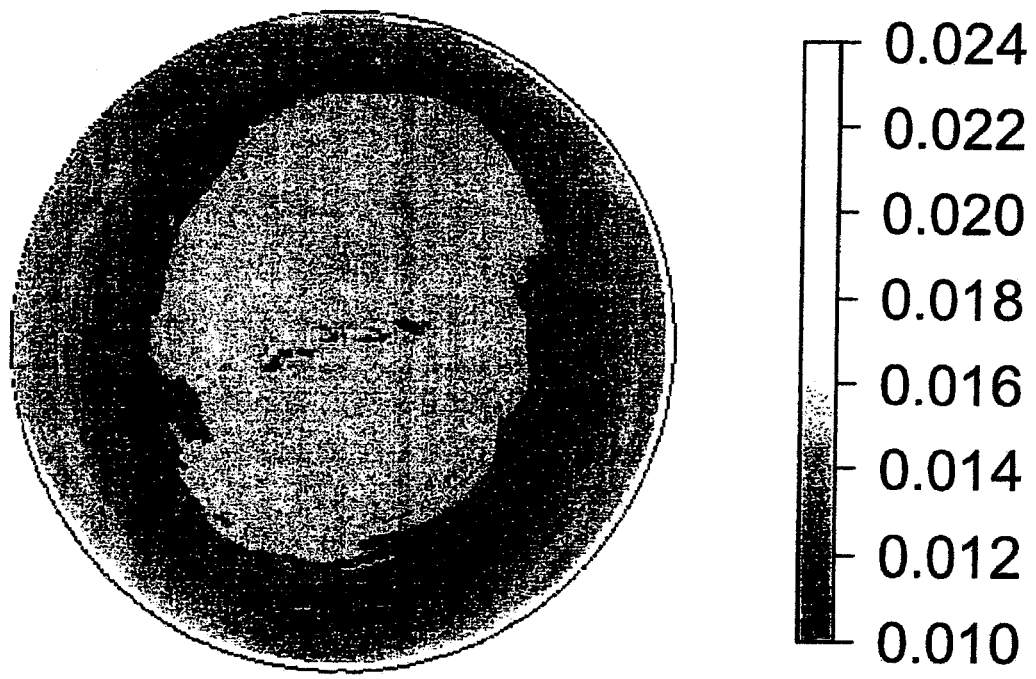

FIG. 16 is an explanatory diagram illustrating saturation of frequency of detected voltage values of the dark-field inspection apparatus in the wafer-surface inspecting process according to the embodiment of the present invention; and FIG. 17 is an explanatory diagram illustrating an example of actually-measured haze values to be output by the dark-field inspection apparatus that inspects a surface of a wafer according to the embodiment of the present invention.

BEST MODE FOR CARRYING OUT THE INVENTION

Prior to detailed descriptions of the invention of the present application, the meanings of terms in the present application are described as follows.

A dark-field inspection apparatus refers to an inspection apparatus that, by using the fact that light is scattered from an asperity surface when asperities on the surface of a test sample are irradiated with light and receiving the scattered light, detects the microscopic asperities on the surface of the test sample. In wafer surface inspection, the apparatus is used to determine a microscopic flaw on the surface (on the order of several tens of Å), asperities, a step height, and the presence or absence of a foreign matter or the like.

A bulk wafer refers to a wafer on which a surface layer serving as a member of a semiconductor device has not yet been formed.

A mirror wafer refers to a wafer mirror-finished with a polishing process, and there are a single-sided mirror wafer with only one surface mirror-finished and a double-sided mirror wafer with both surfaces mirror-finished.

Haze or microhaze refers to a wafer surface state when a mirror wafer is irradiated with light, in which light is scattered in an entire perimeter direction due to roughness (asperities) of a wafer surface. By receiving scattered light, an average value of roughness degrees of haze can be calculated.

Microroughness refers to a surface roughness component in which an asperity distance (a spatial wavelength range $\lambda$) on a wafer surface is less than about 100 μm.

An APM (Ammonia-Hydrogen Peroxide Mixture) solution or SC-1 (RCA Standard Clean 1 (RCA Corporation's standard first cleaning solution)) solution refers to a cleaning solution for silicon wafers at a compounding ratio in volume of ammonia water, a hydrogen peroxide solution, and water (pure water (DIW: De-Ionized Water)) being 1:1:5 to 1:1:50. By immersing a silicon wafer in the APM solution at approximately 40° C. to 90° C., organic dirt or attached particles on the silicon wafer surface can be removed. The APM solution may be used as being added with either one or both of a chelating agent and a surfactant agent.

Here, ammonia has a property of etching (cutting into) a wafer, and a hydrogen peroxide solution has a property of oxidizing a silicon wafer (a property of suppressing etching). In this manner, an aspect of the chemical solutions for use in the present embodiment is that the chemical solutions have a property of etching a wafer and a property of suppressing wafer etching.

HPM (Hydrochloric acid-Hydrogen Peroxide Mixture) solution or SC-2 (RCA Standard Clean 2 (RCA standard second cleaning solution)) solution refers to a cleaning solution for silicon wafers at a compounding ratio in volume of hydrochloric acid, a hydrogen peroxide solution, and water (pure water (DIW)) being 1:1 to 2:5 to 7. By immersing a silicon wafer, metal impurities on surfaces of the silicon wafer can be removed.

SPM (Sulfuric acid-Hydrogen Peroxide Mixture) solution refers to a cleaning solution for silicon wafers formulated with concentrated sulfuric acid and a hydrogen peroxide solution. The SPM solution may be used as being added with either one or both of a surfactant agent and fluoric acid.

DHF (Diluted Hydrofluoric acid) solution refers to a cleaning solution for silicon wafers formed of hydrofluoric acid solution diluted at about 1:100. By immersing a silicon wafer in the DHF solution at ambient temperature, a silicon oxide coating on the surface of the silicon wafer can be removed. The DHF solution may be used as being added with one or more of a surface active agent, a hydrogen peroxide solution, hydrochloric acid, and isopropyl alcohol.

BHF (Buffered Hydrofluoric acid) solution refers to a cleaning fluid for silicon wafers mixed with an ammonium fluoride liquid, fluoric acid, and hydrogen-bonded water ($H_4O$). By immersing a silicon wafer in the BHF solution, a silicon oxide coating on the surface of the silicon wafer can be removed. The BHF solution may be used as being added with one or more of a surfactant agent, a hydrogen peroxide solution, hydrochloric acid, and isopropyl alcohol.

Atomic Force Microscope (AFM) refers to a microscope in which, by using a phenomenon of a gravitational force and a repulse force acting between two bodies coming close to each other, these forces are detected while mechanical scanning is being performed with a microscopic probe close to a test sample, thereby imaging asperities on a surface of the test sample at an atomic and molecular level. Note that the AFM is one type of scanning-type probe microscope.

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specified number is also applicable.

Further, in the embodiments described below, it goes without saying that the components (including element steps) are not always indispensable unless otherwise stated or except the case where the components are apparently indispensable in principle. Also, it is needless to say that, when using "including A," "formed of A," other components are not excluded unless otherwise stated that the component is limited to the mentioned one.

Similarly, in the embodiments described below, when the shape of the components, positional relation thereof, and the like are mentioned, the substantially approximate or similar shapes and the like are included therein unless otherwise stated or except the case where it is conceivable that they are apparently excluded in principle. The same goes for the numerical value and the range mentioned above.

Further, when mentioning material etc., specified materials are main materials and extraneous elements, additive substances, and added component are not excluded unless otherwise stated or the material is not available in principle or in the circumstances. For example, a silicon member includes, unless otherwise stated, not only pure silicon but also an alloy (for example, SiGe) of binary or ternary alloy containing an additional impurity and silicon as main components.

In addition, the description of the same or similar portions is not repeated in principle unless particularly required in the following embodiments.

Also, in some drawings referenced in the embodiments, hatching is used even in a plan view so as to make the drawings easy to see.

Hereinafter, embodiments of the present invention will be described in detail with reference to the accompanying drawings.

First Embodiment

Figure 1:
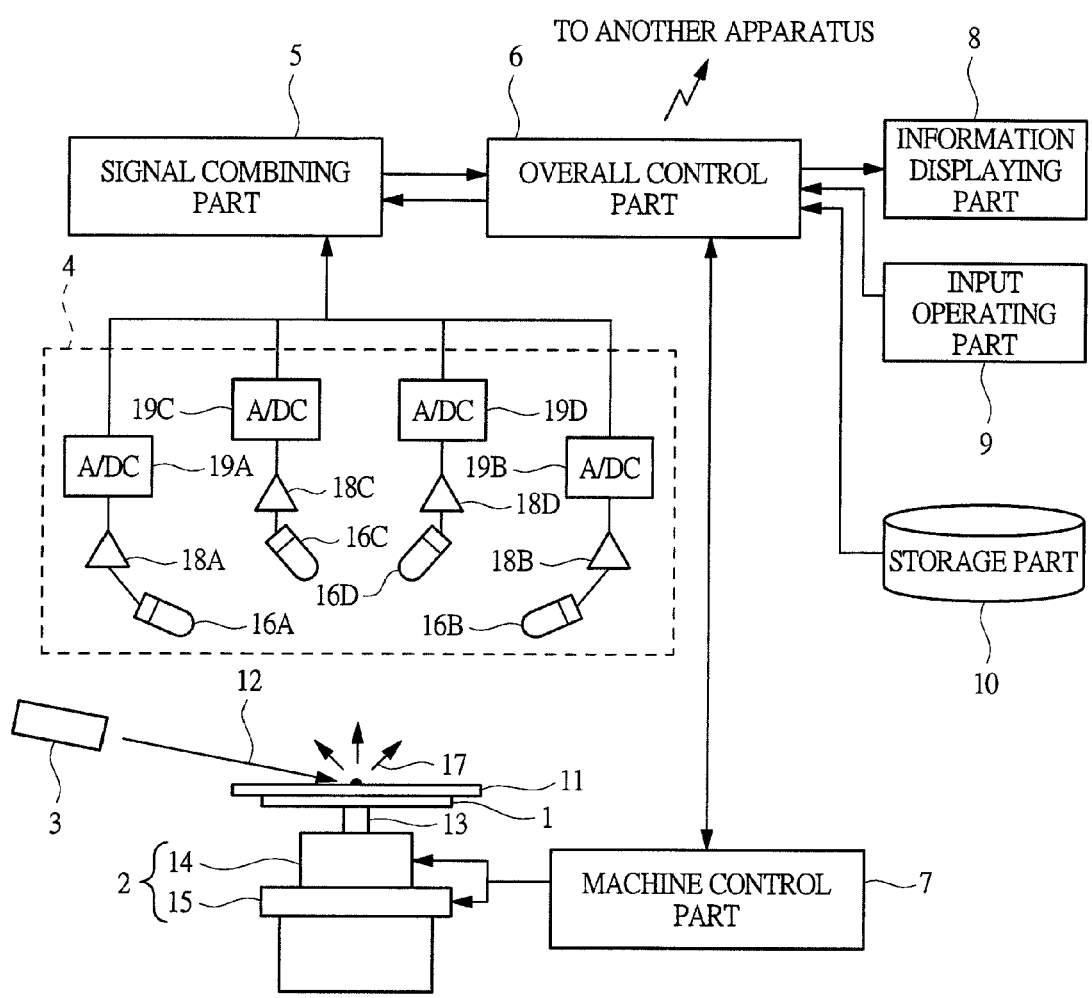
FIG. 1 is an explanatory diagram of a dark-field inspection apparatus which inspects a surface of a wafer according to an embodiment of the present invention.

FIG. 1 is an explanatory diagram of a dark-field inspection apparatus which inspects a surface of a wafer according to an embodiment.

As illustrated in FIG. 1, the dark-field inspection apparatus of the present embodiment includes a test sample stage 1, a stage driving part 2, an illumination light source 3, a scattered-light detecting part 4, a signal combining part 5, a general control part 6, a machine control part 7, an information displaying part 8, an input operating part 9, a storage part 10, and others.

The test sample stage 1 holds a wafer 11 placed thereon, which is a test sample to be inspected. The stage driving part 2 drives the test sample stage 1 so that the wafer 11 is scanned with luminous light 12 emitted from the illumination light source 3 to a fixed point (spot).

The stage driving part 2 includes a rotation driving part 14 that rotates the test sample stage 1 about a rotational shaft 13 and a slide driving part 15 that moves the test sample stage 1 in a diameter direction of the wafer 11. When the wafer 11 on the test sample stage 1 is irradiated with the luminous light 12 by the illumination light source 3, the test sample stage 1 is moved in a diameter direction of the wafer 11 by the slide driving part 15 as being rotated by the rotation driving part 14. With this, the wafer 11 is scanned with the luminous light 12 in a spiral shape.

The scattered-light detecting part 4 has a plurality of detectors 16A to 16D different in position with respect to a spot of the luminous light 12. In FIG. 1, four detectors are illustrated, that is, the detectors 16A and 16B disposed at low angle positions and the detectors 16C and 16D disposed at high angle positions, but the number of the detectors is not limited to this, and two or more detectors can be disposed as long as at least either of their azimuth angles or elevation angles from a luminous light spot are different from each other. Each of the detectors 16A to 16D detects scattered light 17 occurring from the surface of the wafer 11 as the luminous light 12 is emitted from the illumination light source 3. Output from the detectors 16A to 16D includes a defect detection signal (a defect signal) of a high-frequency component and a haze signal of a low-frequency component.

Also, in the scattered-light detecting part 4, the detectors 16A to 16D have connected thereto amplifiers 18A to 18D and A/D converters 19A to 19D, respectively. Detection signals from the detectors 16A to 16D are amplified via the amplifiers 18A to 18D, respectively, and are converted to digital signals via the A/D converters 19A to 19D, respectively.

The signal combining part 5 combines the detection signals from the detectors 16A to 16D, which have been converted to digital signals, according to a specified computing condition (program). The computing condition for a combined signal in the signal combining part 5 is not a fixed condition defined in advance but a condition changeably specified as appropriate by an operator through the input operating part 9. Data of the combined signal obtained by combining by the signal combining part 5 is output to the storage part 10 for storage together with data of the detection signals of the detectors 16A to 16D, on which the combined signal is based. The data includes, for example, individual positions of detected defects (XY coordinates in the plane of the wafer 11, which is a test sample to be inspected), and their sizes. Also, the configuration may be such that the apparatus is connected via a network to, for example, another inspection apparatus and/or manufacturing apparatus, such as an inspection apparatus using an electron microscope, so that the data can be output thereto.

The general control part 6 performs a general control for the apparatus by processing signals regarding display and input and output of information according to operation steps (inspection condition settings, result display, and specification of an analysis and a computing equation). For example, based on an operation signal from the input operating part 9 and a corresponding program stored in the storage part 10, the general control part plays a role of outputting an instruction signal to the machine control part 7 and changing a computing condition for the combined signal in the signal combining part 5. The machine control part 7 controls a driving mechanism, such as the rotation driving part 14 and the slide driving part 15, upon reception of an instruction signal from the general control part 6. In addition, the general control part 6 also plays a role of outputting the combined signal input via the signal combining part 5 and the detection signals from the detectors 16A to 16D to the storage part 10 for recording and generating a display signal to the information displaying part 8 based on these signals to cause an image to be displayed on the information displaying part 8.

The input operating part 9 is to input a condition for combining the detection signals by the signal combining part 5 and to give instructions for the operation of each part and others, as described above.

The information displaying part 8 displays a test sample image constructed based on the combined signal obtained by combining in the signal combining part 5 according to the condition specified by the input operating part 9 (hereinafter, referred to as a combined test sample image), a plurality of test sample images corresponding to the individual detectors constructed based on the detection signals from the corresponding detectors (hereinafter, referred to as individual test sample images), detected data, a detection condition (recipe), and others. For example, the inspection results are displayed after an inspection is over, and the combined test image and the individual test sample images are displayed on the same screen during an analysis. The combined test sample image and the individual test sample images may be switchably displayed.

The storage part 10 has stored therein programs, constants, and inspection results (data of the combined test sample image and the individual test sample images) required for various control and computing processes, the combining condition set by the input operating part 9, and others. The data of the individual test sample images is stored for each of the detectors 16A to 16D together with address information of the detectors.

As described above, the detection signals are combined by the signal combining part 5 according to the condition set by the operator through the input operating part 9. This setting can be changed as appropriate according to an input operation of the input operating part 9.

What the dark-field inspection apparatus of the present embodiment as described above inspects is a surface of a so-called bulk wafer (a first bulk wafer), which can be exemplified by a bulk wafer of single crystal silicon. This is because, for example, when a thin film layer, such as an epitaxial layer, is formed on the surface, regular asperities are formed on the surface, and when the wafer 11 is irradiated with the luminous light 12 described above, a unique optical pattern appears instead of desired haze, due to thin-film interference caused by crystal orientation and others not relevant to an asperity state, which makes it impossible to obtain accurate measurement results. For this reason, a target whose surface is to be inspected by the dark-field inspection apparatus of the present embodiment is preferably a bulk wafer.

Figure 2:
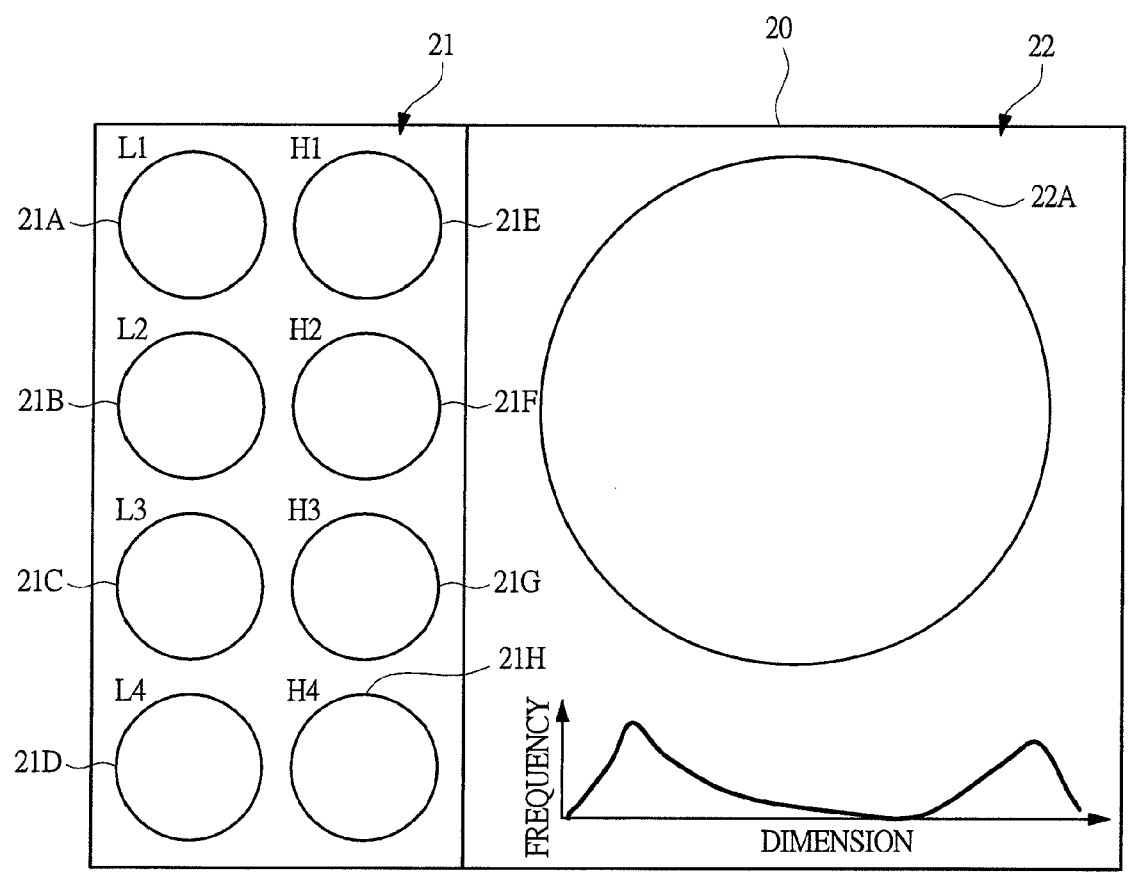
FIG. 2 is an explanatory diagram illustrating an example of an analysis screen displayed on an information displaying part of the dark-field inspection apparatus illustrated in FIG. 1.

FIG. 2 is an explanatory diagram illustrating an example of an analysis screen displayed on the information displaying part 8.

As illustrated in FIG. 2, on an analysis screen 20, a display area 21 for eight individual maps 21A to 21H and a display area 22 for an enlarged map 22A where a selected one of the individual maps 21A to 21H is displayed in an enlarged manner are disposed. In the example illustrated in FIG. 2, it is assumed that the scattered-light detecting part 4 (refer to FIG. 1) includes eight detectors, that is, low-angle detectors L1 to L4 disposed at four orientations and high-angle detectors H1 to H4 disposed at four orientations.

On the individual map 21A, a defect detected by the corresponding low-angle detector L1 is displayed in a shape of an individual test sample image displayed so as to be superposed on a wafer map. Similarly, on each of the individual maps 21B to 21H, an individual test sample image is displayed based on a corresponding one of the detectors L2 to L4 and H1 to H4. The individual maps 21A to 21H may be displayed in an arrangement corresponding to the actual layout of the detectors L1 to L4 and H1 to H4.

On the enlarged map 22A, any one of the individual maps 21A to 21H selected through an input operation with the input operating part 9 (refer to FIG. 1) or through a touching operation on one of the individual maps 21A to 21H is displayed in an enlarged manner. Also, in a lower area of the enlarged map 22A in the analysis screen 20, a histogram of dimensions of a defect displayed on the enlarged map 22A is displayed.

In this manner, the enlarged map 22A and the histogram can be sequentially checked for each of the individual maps 21A to 21H to check a defect distribution for each dimension, and determine a difference in range of noise levels. Also, by displaying the individual maps 21A to 21H on the analysis screen 20 on a list, the tendency of dependence of the defect distribution on a detector orientation can also be identified.

Meanwhile, to accurately detect the defect distribution, it is desired to accurately calibrate the dark-field inspection apparatus in advance to ensure the measurement results. In particular, in semiconductor device manufacture, even a slight change in microroughness on a surface of a wafer may invite a deterioration in characteristics. Therefore, the quality of the wafer surface is required to be ensured by detecting microscopic defects on the wafer surface.

Figure 3:
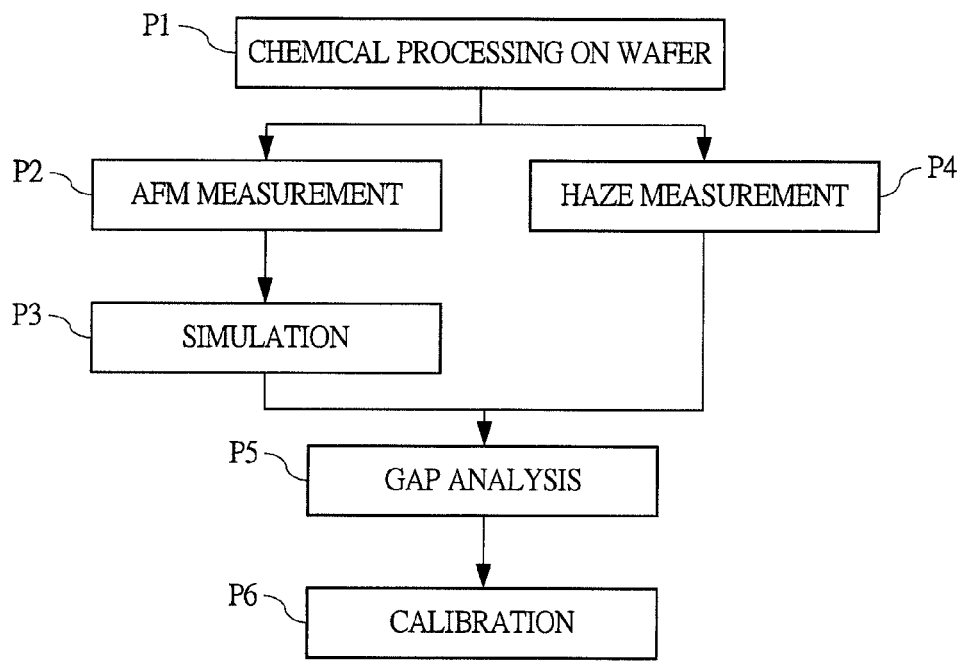
FIG. 3 is a flowchart describing a general outline from providing a bulk wafer serving as a reference wafer for use in calibration of the dark-field inspection apparatus illustrated in FIG. 1 to performing calibration of the dark-field inspection apparatus.

Thus, in the present embodiment, the dark-field inspecting apparatus is first calibrated by using a bulk wafer (a second bulk wafer) as a reference wafer, in which microroughness of an irregular (random) asperity pattern is accurately formed on its surface and the roughness degree of the microroughness on the surface is ensured. Here, FIG. 3 is a flowchart for describing a general outline from preparing a bulk wafer serving as a reference wafer to performing calibration of the dark-field inspection apparatus.

Figure 4:
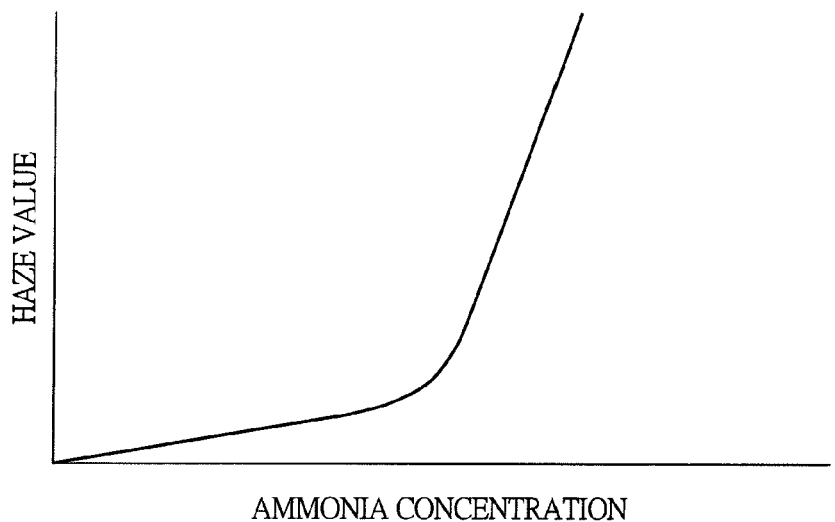
FIG. 4 is an explanatory diagram illustrating a relation between concentration of ammonia in an APM fluid and haze formed on a mirror wafer.

The bulk wafer as a reference wafer described above is a mirror wafer. The surface of this mirror wafer is subjected to a chemical treatment using a chemical solution so as to have microroughness accurately formed thereon (process P1). Here, when the bulk wafer is formed of single crystal silicon, one or more of an APM solution (SC-1 solution), an HPM solution (SC-2 solution), an SPM solution, a DHF solution, a BHF solution, a mixed aqueous solution of fluoric acid and ozone water (on the order of 1% concentration of fluoric acid) can be exemplarily selected for use as a chemical solution. For example, when an APM solution is used, by controlling either one or both of the concentration of ammonia in the AMP solution and a time period of contact between the mirror wafer and the APM solution, microroughness of an irregular asperity pattern can be accurately formed on the surface of the mirror wafer at a desired roughness degree. That is, desired haze corresponding to this microroughness can be accurately created (refer to FIG. 4). The desired roughness degree of microroughness is about 0.1 nm, for example, which is problematic in semiconductor device manufacture. In the microroughness (haze) formed in this manner, a change with time in shape tends not to occur, thereby keeping a surface state.

On the other hand, when a mixed aqueous solution of fluoric acid and ozone water is used as the chemical solution described above, formation of an oxidation layer on the surface of the mirror wafer using ozone water and etching of the oxidation layer using fluoric acid occur simultaneously to form microroughness. Here, a process of forming an oxidation layer using ozone water and a process of etching the oxidation layer using diluted fluoric acid are performed separately, so that oxidation and etching can be separately controlled. By using this way, the roughness degree of microroughness can be accurately controlled.

Next, by using the AFM, the roughness degree of microroughness formed in the above process P1 is measured (process P2). Here, as an area for measurement with the AFM, an area equal to or larger than a beam diameter of the AFM is set. Also in consideration of error in measured coordinates, an area within several $mm^2$ where an abrupt change is not observed (a portion where a local peak is not present) is selected so that a histogram, a cross-section waveform, and a distribution of detection amounts, which will be described further below, can be identified. After measurement with the AFM, it is confirmed in a measured profile that asperities in a spike shape due to a flaw or a foreign substance on the surface of the mirror wafer are not present. The reason for this confirmation is that such asperities in a spike shape are out of the presumption for a simulation in the next process and therefore do not bring a match with the detection amount from the dark-field inspection apparatus.

Next, a simulation is performed based on the roughness degree of microroughness measured in the process P2 to obtain a simulation value of haze created on the surface of the mirror wafer, that is, an expected haze value (process P3). Here, a BRDF (Bidirectional Reflectance Distribution Function) value is calculated based on the roughness degree of microroughness measured in the process P2. The BRDF value represents a ratio (Idet/Iin) between the scattered light 17 (Iin) and the luminous light 12 (Idet). From this BRDF value and various parameters of the dark-field inspection apparatus, an expected haze value is calculated.

Here, calculation of the BRDF value mentioned above will be described in further detail.

Measurement of a roughness degree of microroughness by the AFM in the process P2 is performed with defining an X direction and a Y direction orthogonal to the X direction in a measurement area. In the process P3, for each value of a roughness degree of microroughness measured in the process P2, a change in the roughness degree of microroughness in the X direction with respect to each Y position is subjected to a linear Fourier transform. Then, the results of this linear Fourier transform are averaged in the Y direction, are fitted to a PSD (Power Spectrum Density) function S(f), which is a function of a spatial frequency f, thereby determining each parameter (constant) of the PSD function S(f). This is because a relation between the intensity of the scattered light when the microroughness is irradiated with light and the spatial frequency is equal to the PSD function S(f) obtained through the linear Fourier transform. In this manner, based on the PSD function S(f) with each parameter determined, the roughness degree of microroughness measured by the AFM is converted to a PSD light amount (in units of W). Next, based on this PSD light, a power density equivalent to an amount of light entering each of the detectors (16A to 16D), that is, photomultiplier tubes (PMTS), is converted to an electrical signal. Next, based on the power density converted to an electrical signal, a conversion to an output current is performed in consideration of a gain obtained from a voltage to be applied to each of the photomultiplier tubes. Then, the current value is converted to a voltage value by each of the amplifiers (18A to 18D), the voltage value is converted to a digital value to be output from each of the A/D converters (19A to 19D), and then these digital values are combined to obtain the expected haze value described above. Next, haze on the surface of the reference wafer with microroughness formed thereon is measured by the dark-field inspection apparatus to be calibrated, and an actually-measured haze value is obtained (process P4). In actual measurement of haze, the surface of the reference wafer is irradiated with the luminous light 12 from the illumination light source 3, and scattered light occurring from the surface of the reference wafer is detected. The detectors (16A to 16D) receive the scattered light to output a current, and the amplifiers (18A to 18D), each of which outputs an output voltage corresponding to a current value output from a corresponding one of the detectors (16A to 16D). Furthermore, the voltage values are converted to digital values by the A/D converters (19A to 19D), and the digital values are combined by the signal combining part 5, thereby outputting an actually-measured haze value. Next, a difference between the expected haze value obtained in the process P3 and the actually-measured haze value obtained in the process P4 is obtained (process P5) and, based on this difference, haze measurement parameters of the dark-field inspection apparatus are adjusted so that the actually-measured haze value and the expected haze value match each other (process P6).

The processes P1 to P4 will be individually described in further detail below.

In calibrating the dark-field inspection apparatus, not only the detection accuracy for a certain point, for example, the microroughness (haze) of about 0.1 nm described above, is calibrated, but also detection accuracy for a predetermined wide range of numerical values, for example, microroughness (haze) of about 0.1 nm to 1.0 nm, is calibrated. To do this, in the process P1, for example, a plurality of mirror wafers are provided, and microroughness with a different roughness degree is formed on each wafer. In the present embodiment, three or more mirror wafers are provided, and roughness degrees of microroughness are set between about 0.1 nm to 1.0 nm in fixed-value increments as many as the number of mirror wafers, and microroughness at each degree is formed on each of the mirror wafers. That is, different microroughness (haze) is formed for each mirror wafer. Therefore, the roughness degree (magnitude) of microroughness is measured by the AFM for each mirror wafer in the process P2; an expected haze value is obtained for each mirror wafer in the process P3; an actually-measured haze value is obtained for each mirror wafer in the process P4; and a difference between the expected haze value and the actually-measured haze value is obtained for each mirror wafer in the process P5. Such a way of using a plurality of mirror wafers as described above will be described more below with reference to FIG. 5.

Also, instead of using a plurality of mirror wafers and forming microroughness of a different roughness degree for each mirror wafer, for example, the surface of one mirror wafer may be sectioned into a plurality of areas (haze areas) and microroughness of a roughness degree set at every fixed value described above may be formed on each area. That is, different microroughness (haze) is formed for each sectioned area on the surface of the one mirror wafer. Therefore, the roughness degree (magnitude) of microroughness is measured by the AFM for each sectioned area in the process P2; an expected haze value is obtained for each sectioned area in the process P3; an actually-measured haze value is obtained for each sectioned area in the process P4; and a difference between the expected haze value and the actually-measured haze value is obtained for each sectioned area in the process P5. The way of using a mirror wafer with a surface sectioned in a plurality of areas will be further described below with reference to FIG. 6.

Here, the actual measurement of haze by the dark-field inspection apparatus in the above-described process P4 will be described in further detail with reference to FIGS. 5 and 6.

As described above, FIG. 5 illustrates the case of performing actual measurement of haze by the dark-field inspection apparatus using a plurality of reference wafers, in which three reference wafers 23A to 23C are used. These reference wafers 23A to 23C are accommodated in slots 1 to 3, respectively, of the dark-field inspection apparatus. Also, the roughness degrees of microroughness formed on surfaces of the reference wafers 23A to 23C are decreased in the order of the reference wafers 23A, 23B, and then 23C.

In the actual measurement of haze, a target area is set on the surface of each of the reference wafers 23A to 23C, and output voltages are measured at a plurality of positions in the target area. Here, output voltage values to be output are numerical values obtained by combining in the signal combining part 5. Then, a histogram is created from the obtained output voltage values; an output voltage value representing a most frequent value is taken as a detected voltage value; and this detected voltage value is converted to a haze value. Note that FIG. 5 also illustrates expected haze values (a voltage value before conversion) in addition to these detected voltage values and haze values.

Figure 6:
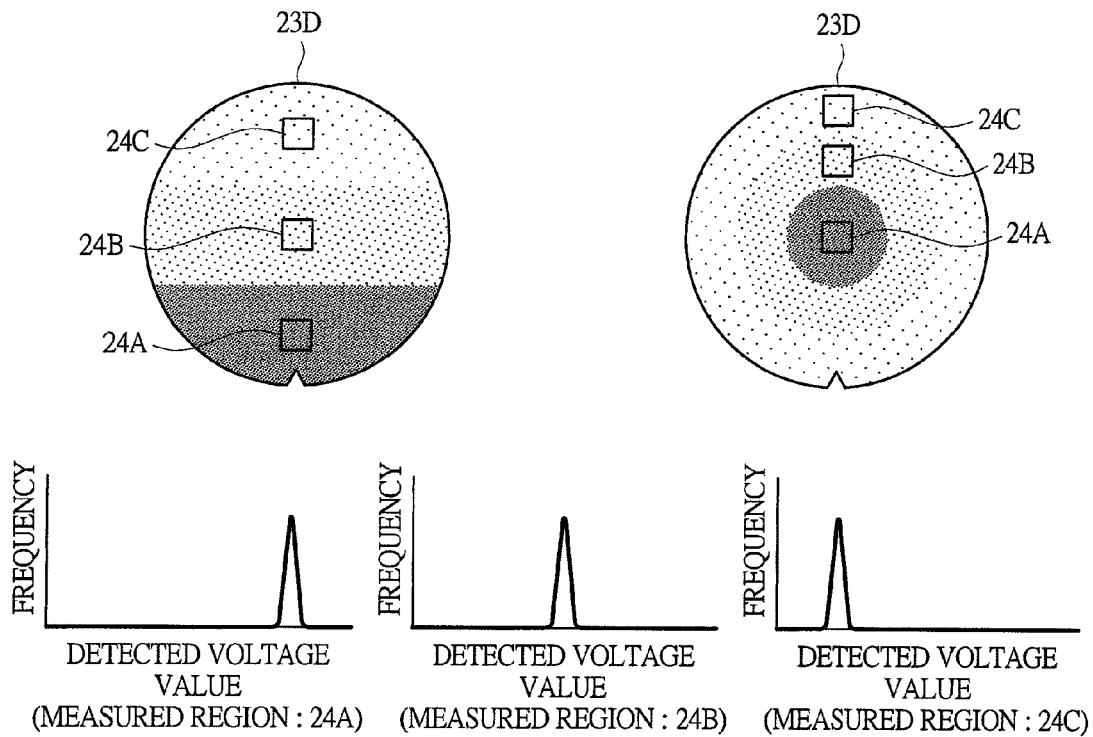
FIG. 6 is an explanatory diagram illustrating haze measurement using one reference wafer sectioned in a plurality of areas having microroughness of different degrees of roughness formed thereon.

Meanwhile, FIG. 6 illustrates the case of performing actual measurement of haze by the dark-field inspection apparatus using one reference wafer 23D sectioned into a plurality of areas (haze areas) on a surface.

When the surface is sectioned into a plurality of areas (haze areas), there are an example of sectioning in a band-like fashion, the bands being parallel to each other (in the case of the reference wafer 23D on the left in FIG. 6), and an example of sectioning in a concentric fashion from the center of the reference wafer 23D (in the case of the reference wafer 23D on the right in FIG. 6). In the case of sectioning in a concentric fashion, there is no clear difference in the roughness degrees of microroughness at each boundary of areas, and a reason for that will be described further below together with a method of forming the reference wafer 23D. In the example illustrated in FIG. 6, three areas (haze areas) having different roughness degrees of microroughness are formed on the surface of the reference wafer 23D. In the respective areas, target areas 24A to 24C are set for haze measurement. The roughness degrees of microroughness are set in, for example, a decreasing order of the target areas 24A, 24B, and then 24C.

Figure 5:
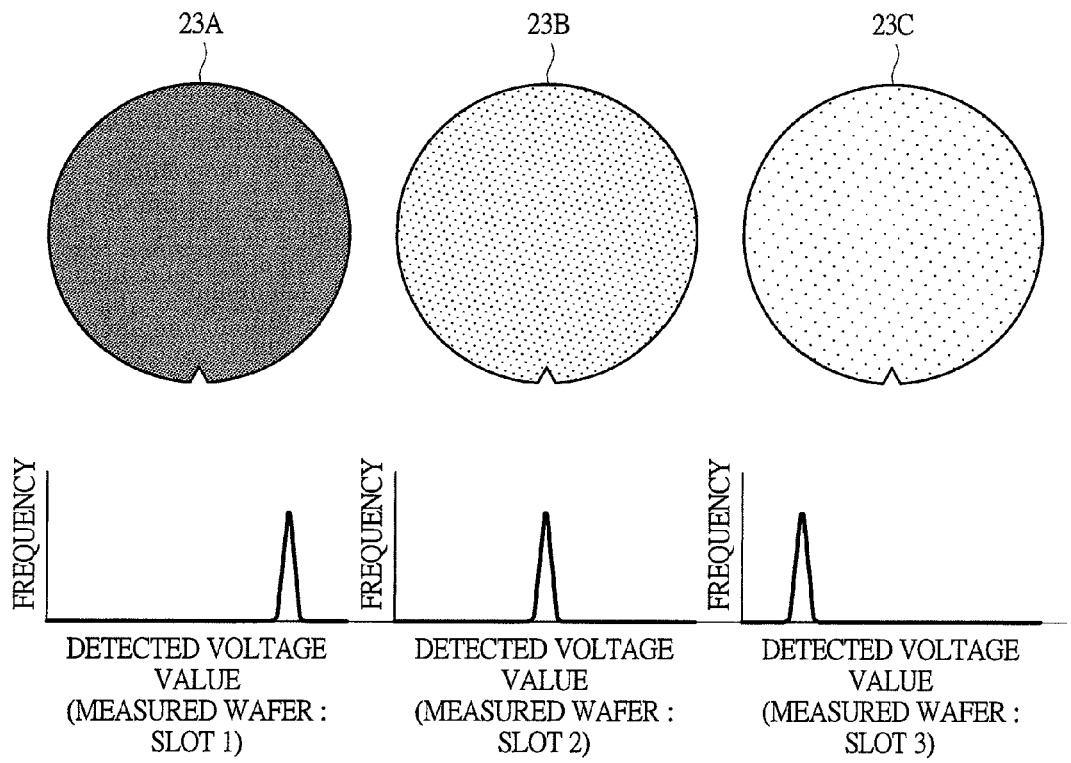
FIG. 5 is an explanatory diagram illustrating haze measurement using a plurality of reference wafers having microroughness of different degrees of roughness formed thereon.

As described in the case of using the plurality of reference wafers 23A to 23C illustrated in FIG. 5, in the actual measurement of haze, output voltages are measured at a plurality of positions in each of the target areas 24A to 24C. Here, output voltage values to be output are numerical values each obtained by combining in the signal combining part 5. Then, a histogram is created from the output voltage values obtained for each of the target areas 24A to 24C; an output voltage value representing a most frequent value is taken as a detected voltage value; and this detected voltage value is converted to a haze value. Note that FIG. 6 illustrates expected haze values (voltage values before conversion) in addition to these detected voltage values and haze values. In this manner, when one reference wafer 23D having the surface sectioned into a plurality of areas (haze areas) is used, compared with the case of using the plurality of reference wafers 23A to 23C, time required for the reference wafer (s) to be loaded to and unloaded from the dark-field inspection apparatus and time required for actual measurement of haze can be reduced. Therefore, when the dark-field inspection apparatus is regularly calibrated, an effect of reducing calibration time can be particularly achieved.

Figure 7:
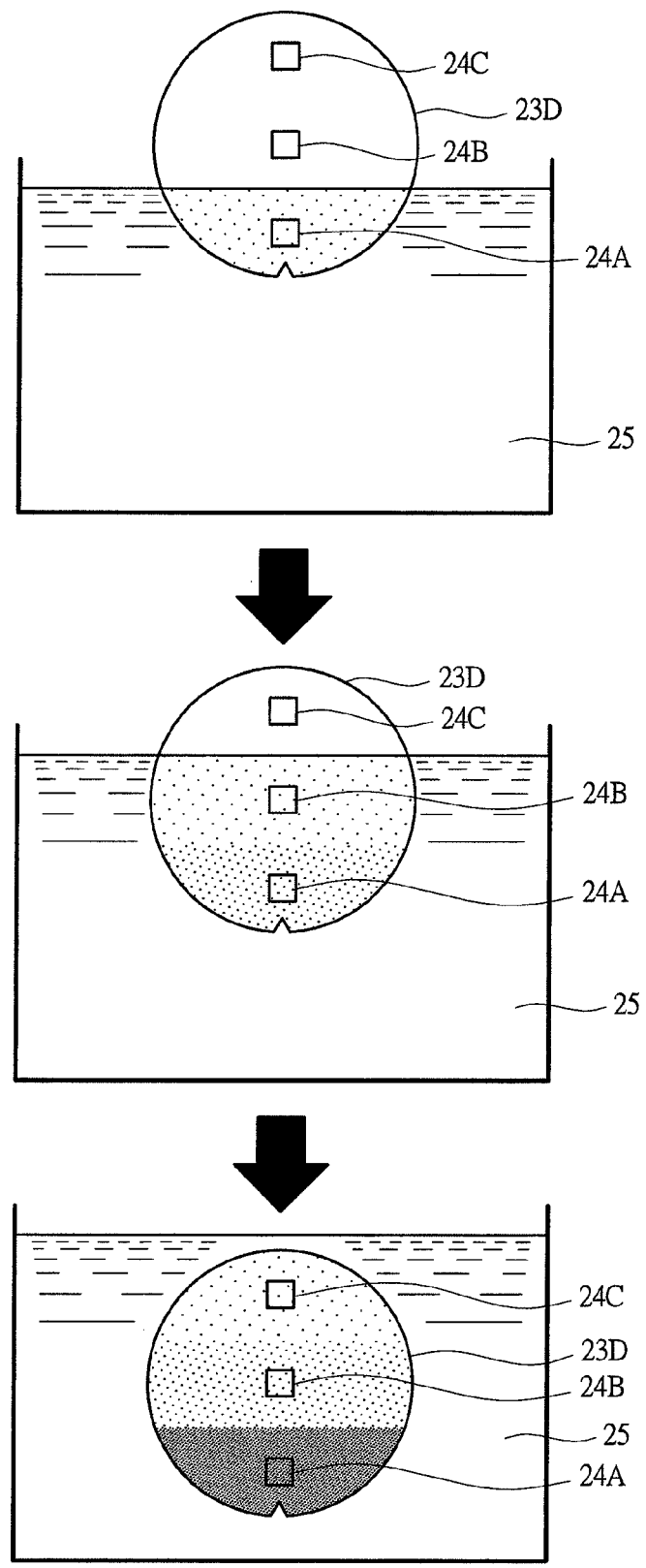
FIG. 7 is an explanatory diagram illustrating means for forming microroughness of a different degree of roughness for each of a plurality of areas obtained by sectioning the reference wafer.
Figure 8:
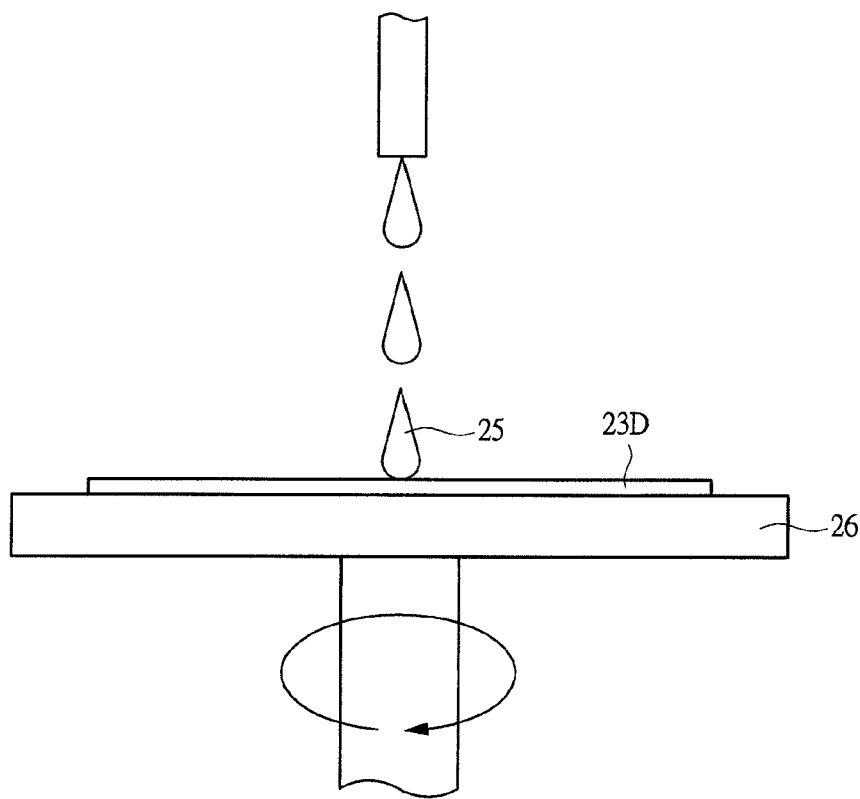
FIG. 8 is an explanatory diagram illustrating means for forming microroughness of a different degree of roughness for each of a plurality of areas obtained by sectioning the reference wafer.

Here, a method of creating the reference wafer 23D illustrated in FIG. 6 is described with reference to FIGS. 7 and 8. FIG. 7 illustrates the case of sectioning into a plurality of areas (haze areas) in band shapes parallel to each other, and FIG. 8 illustrates the case of sectioning in a plurality of areas (haze areas) in a concentric fashion from the center of the reference wafer 23D.

As illustrated in FIG. 7, in the case of sectioning into a plurality of areas (haze areas) in band shapes parallel to each other, only a area where the target area 24A is to be set (a first haze area) in the reference area 23D is first immersed for a predetermined time in a chemical solution 25 as described above for forming microroughness on the surface of the reference wafer 23D, thereby forming microroughness in only the area where the target area 23A is to be set. However, here, the roughness degree of microroughness formed in the area where the target area 24A is to be set is not the same as a roughness degree of microroughness eventually formed in the area where the target area 24A is to be set. Next, only the areas where the target areas 24A and 24B are to be set in the reference wafer 23D are immersed for a predetermined time in the chemical solution 25, thereby forming microroughness in the area where the target area 24B is to be set (a second haze area), thereby making the microroughness formed in the area where the target area 24A is to be set rougher. Next, the entire reference wafer 23D is immersed for a predetermined time in the chemical solution 25, thereby forming microroughness in an area where the target area 24C is to be set and making the microroughness formed in the areas where the target areas 24A and 24B are to be set rougher. In the processes so far, microroughness of a desired roughness degree can be formed in each of the plurality of areas (haze areas) including the target areas 24A to 24C, respectively. Here, although the method of forming microroughness in the case of sectioning into three reference areas (haze areas) on the reference wafer 23D has been exemplarily described, similar processes can be used with more steps to immerse the reference wafer 23D in the chemical solution 25 even in the case of sectioning into many more areas (haze areas).

In the case of sectioning into a plurality of areas (haze areas) in a concentric fashion from the center of the reference wafer 23D. As illustrated in FIG. 8, the reference wafer 23D is placed on a turn table (rotational stage) 26. Next, by rotating the turn table 26, a drop of the chemical solution 25 is put on the center of the reference wafer 23D under the state in which the turn table 26 is rotating. Then, as a result of centrifugal force, the chemical solution 25 is spread toward an outer circumference direction of the reference wafer 23D. Since the centrifugal force acts more as it is closer to the outer circumference of the reference wafer 23D, the chemical solution 25 cannot stay longer on the reference wafer as it is closer to the outer circumference of the reference wafer 23D. Therefore, a chemical reaction between the chemical solution 25 and the reference wafer 23D proceeds more in a place closer to the center of the reference wafer 23D, and microroughness at a higher roughness degree is formed in a place closer to the center of the reference wafer 23D, and, at a boundary between areas (haze areas), there is no clear difference in roughness degree of microroughness. That is, by continuing rotation of the turn table 26 and dripping the chemical solution 25 for a predetermined time, microroughness of a desired roughness degree can be formed in each of the plurality of areas (haze areas) including the target areas 24A to 24D, respectively.

Figure 9:
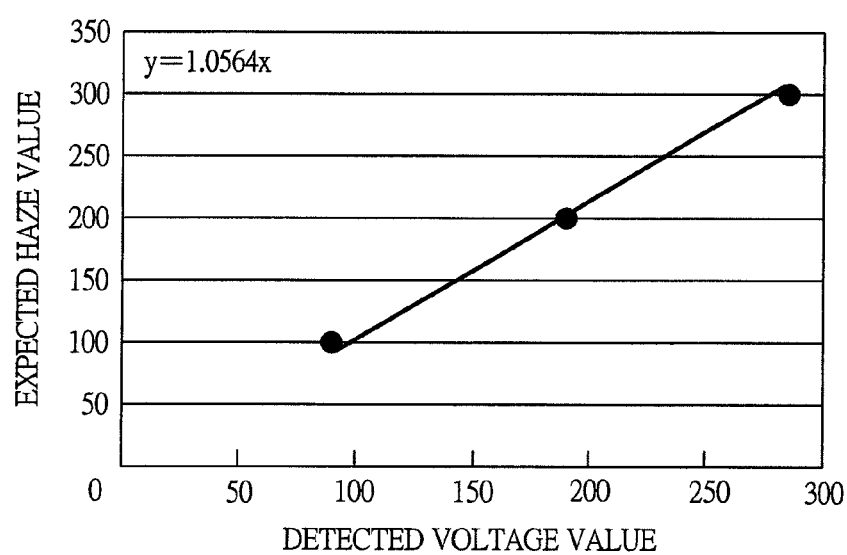
FIG. 9 is an explanatory diagram illustrating normalization of a relation between a detected voltage value and an expected haze value for the reference wafer used in calibration of a dark-field inspection apparatus that inspects a surface of a wafer according to an embodiment of the present invention.

As described above, from the detected voltage values and expected haze values (voltage values before conversion) at a plurality of measurement points obtained through actual measurement in the target areas 24A to 24C on the plurality of reference wafers 23A to 23C or one reference wafer 23D, the detected voltage values are normalized (refer to FIG. 9). This normalizing process corresponds to the above-described process P5.

Second Embodiment

In a second embodiment, the actual measurement of haze by the dark-field inspection apparatus in the process P4 to the adjustment of haze measurement parameters by the dark-field inspection apparatus in the process P6 described with reference to FIG. 3 in the first embodiment described above will be described in further detail with reference to FIGS. 11 to 16.

First, a function of extracting and checking a haze value corresponding to an AFM measurement area, which represent a function and information required for the dark-field inspection apparatus for calibration, information required for performing calibration, and an output unit of the haze value will be described.

Figure 10:
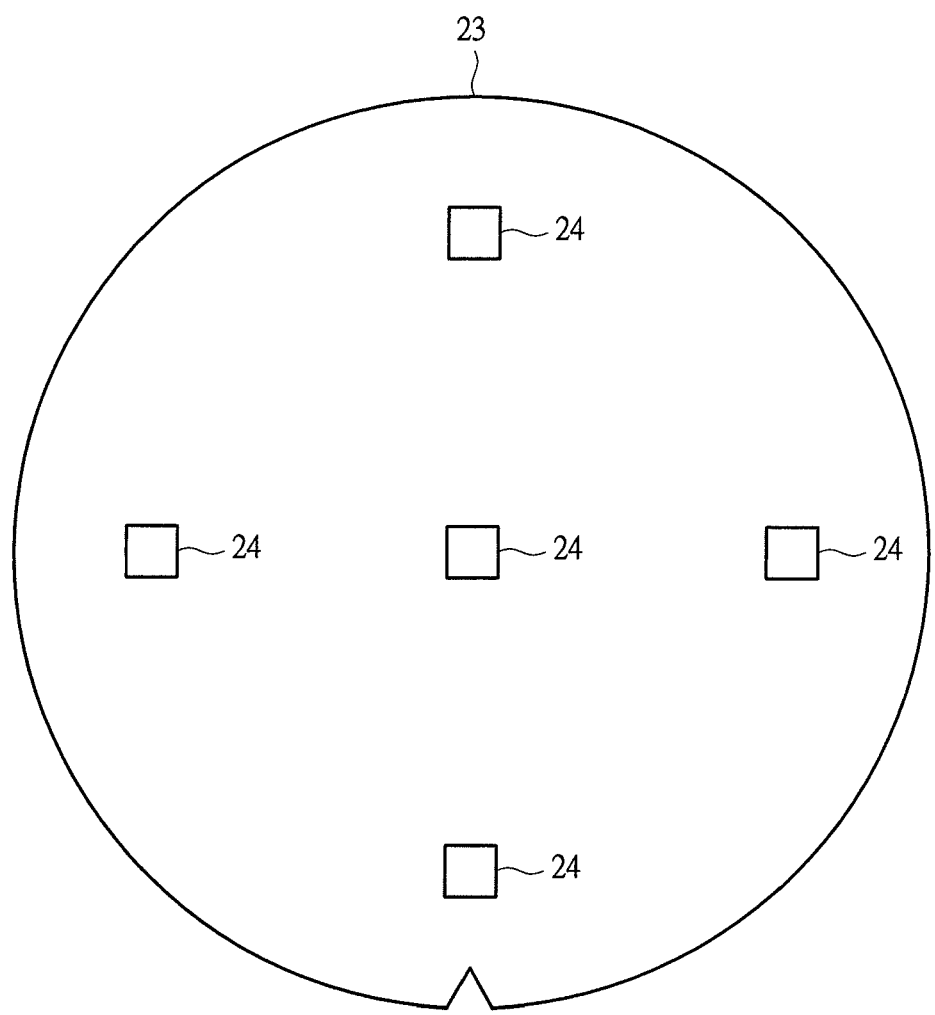
FIG. 10 is an explanatory diagram illustrating a target area on the reference wafer for calibration of the dark-field inspection apparatus that inspects a surface of a wafer according to an embodiment of the present invention.

As a function of extracting and checking a haze value corresponding to an AFM measurement area, there are a function of specifying a target area, such as the target areas 24A to 24C described above (refer to FIG. 6) and a function of outputting a statistical amount in that target area. In the function of specifying a target area, for example, to a reference wafer 23 similar to the reference wafers 23A to 23D described above, an outer shape of a target area 24 and the number of settings in the reference wafer 23 are specified (refer to FIG. 10). Although FIG. 10 illustrates an example in which five rectangular target areas 24 are set in a cross fashion so as to include the center of the reference wafer 23, the respective target areas 24 may be formed in another shape, such as a circle. In the function of outputting a statistical amount in the target area, for example, a maximum value, a minimum value, a standard deviation, a histogram, a most frequent value (peak value) of the histogram of the detected voltage values, and a distribution of the detected voltage values are output.

Information required for calibration includes reference values and are information for calibration of a digitally-converted value output from the signal combining unit 5. The area information includes reference wafer information including lot information of the reference wafer and slot information in the dark-field inspection apparatus in which the reference wafer is accommodated and coordinate information of a plurality of target areas for comparison between an expected haze value and an actually-measured haze value. The reference values include an expected haze value and an actually-measured haze value (a correlation table between BRDF values and RMS (Root Mean Square) values) in the relevant target area.

The haze values are output by converting the detected voltage values of the detectors 16A to 16D as described above. Also, the BRDF values are of an output type of haze values. The BRDF values are calculated from a simulation with the expected haze values and the configuration of the dark-field inspection apparatus described above to have a conversion table with the detected voltage values described above, thereby being output as haze values. Also, once a correlation between the BRDF values and the RMS values can be obtained, a correlation between the detected voltage values and the RMS values can be taken.

Figure 11:
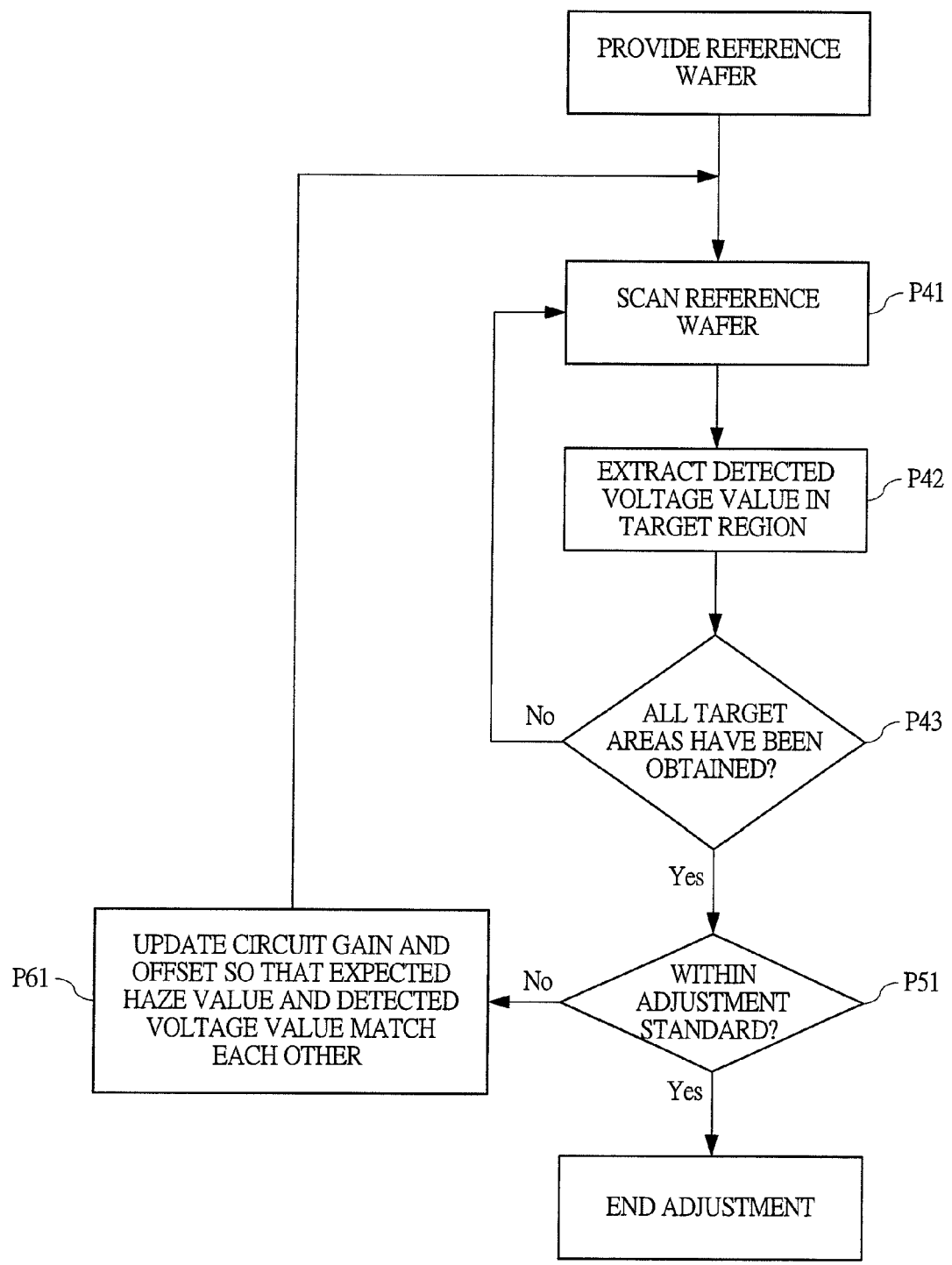
FIG. 11 is a flowchart describing main parts in a calibrating process of the dark-field inspection apparatus that inspects a surface of a wafer according to the embodiment of the present invention.
Figure 12:
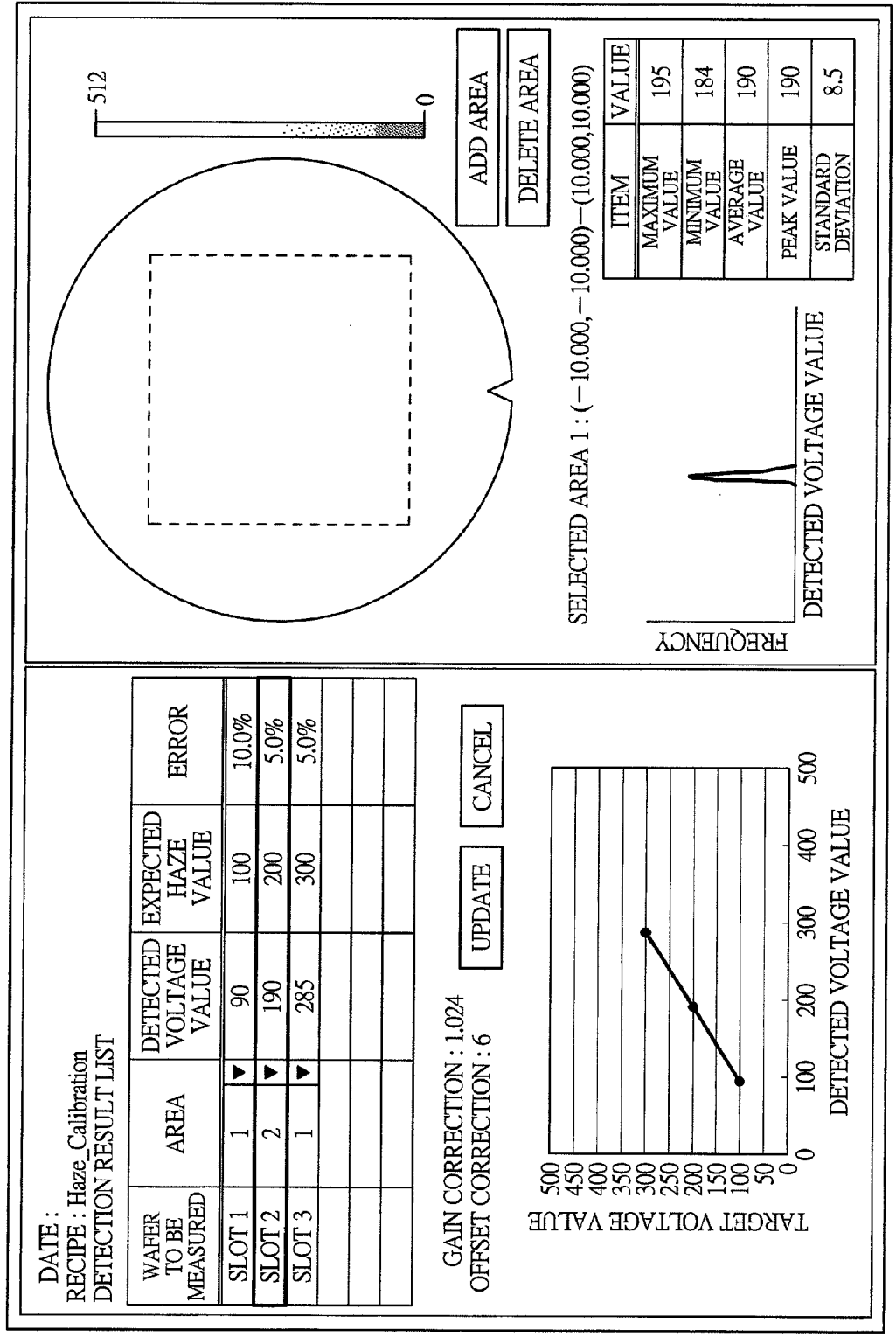
FIG. 12 is an explanatory diagram illustrating display contents of the information displaying part of the dark-field inspection apparatus at the time of the calibrating process of the dark-field inspection apparatus that inspects the surface of a wafer according to the embodiment of the present invention.

FIG. 11 is a flowchart illustrating, in further detail, from the process of actually measuring haze by the dark-field inspection apparatus in the process P4 described in the first embodiment above with reference to FIG. 3 to the process of adjusting a haze measurement parameter of the dark-field inspection apparatus in the process P6, and FIG. 12 is an explanatory diagram illustrating display details of the information displaying part 8 of the dark-field inspection apparatus in the processes.

In the process P4, the target area set on a surface of the reference wafer is first scanned with the luminous light 12 (process P41), and the scattered light 17 is detected by the detectors 16A to 16D, thereby extracting detected voltage values in that target area and outputting the results (process P42).

When the results are output in the above-described process P42, the measured reference wafer (slot number or lot number), the target area, the detected voltage value, the expected haze value (converted voltage value), and an error between the detected voltage value and the expected haze value are displayed. Furthermore, from these displayed detection results, correction values for a gain component and an offset component of a haze signal detection circuit of the dark-field inspection apparatus are shown. At this stage, upon confirming that each output data does not indicate an abnormal value due to a flaw or a foreign substance on the reference wafer, a user of the dark-field inspection apparatus presses an update button of the dark-field inspection apparatus, then the dark-field inspection apparatus stores the correction values for the gain component and the offset component as unique information of the dark-field inspection apparatus. Also, as the user can confirm the histogram of the detected voltage values in the target area and various statistical information on the information displaying part 8 of the dark-field inspection apparatus as illustrated in FIG. 12, at this stage, when an abnormal value due to a flaw or a foreign substance on the reference wafer is obtained, a target area can be reset for another measurement. Furthermore, even if the correction values for the gain component and the offset component in the target area where an abnormal value is obtained have already been stored as unique information of the dark-field inspection apparatus, the information can be deleted by selecting a target area and pressing a delete button of the dark-field inspection apparatus.

As described above, according to the present embodiment, when an abnormal value due to a flaw or a foreign substance on the reference wafer is obtained, a target area can be reset for another measurement; therefore, in addition to a flaw or a foreign substance, even if microroughness of a desired roughness degree has not yet been achieved on the surface, a target area can be reset for another measurement.

Next, it is determined whether results including actually-measured haze values in all target areas have been obtained (process P43). Upon obtainment of the results from all target areas, it is determined whether an error between an actually-measured haze value and an expected haze value is converged within adjustment reference values (process P51). When the error between a detected voltage value and an expected haze value is not converged within the adjustment reference values, calibration is performed based on the correction values for the gain component and the offset component of the haze signal detection circuit in the dark-field inspection apparatus (process P61), and Then, the process of the processes P41 to P51 is again repeated. When the error between a detected voltage value and an expected haze value is converged within the adjustment reference values, calibration of the voltage values is completed.

Through the processes as described above, calibration of the dark-field inspection apparatus of the present embodiment is completed.

According to the present embodiment described in the foregoing, using a reference wafer having microroughness of an irregular asperity pattern accurately formed on a surface with a desired roughness degree, calibration of the dark-field inspection apparatus is performed in the processes as described above, thereby ensuring measurement capability of the dark-field inspection apparatus up to a microscopic area. As a result, when an inspection of a surface of a wafer for semiconductor device manufacture is performed, the inspection results can be ensured up to microscopic values.

Also, according to the present embodiment described in the foregoing, since measurement capability of the dark-field inspection apparatus can be ensured up to a microscopic area, regular calibration of the dark-field inspection apparatus enables it to detect and adjust a microscopic change in measurement capability with time.

Furthermore, according to the present embodiment described in the foregoing, a calibration curve for use in calibration of the dark-field inspection apparatus is obtained based on the results of measuring the roughness degree of microroughness on the surface of the reference wafer by the AFM, thus, by adjusting the output voltage values based on this calibration curve, calibration of the dark-field inspection apparatus is performed. That is, in a state where calibration is performed using the same reference wafer, the output voltage values match each other among a plurality of dark-field inspection apparatuses. In this manner, differences in measurement capability among dark-field inspection apparatuses of the same model can be reduced.

Third Embodiment

In a third embodiment, a process of inspecting a surface of a wafer for semiconductor device manufacture by using the reference wafer for calibration of dark-field inspection apparatuses and the dark-field inspection apparatus calibrated in the calibrating process described in the first and second embodiments described above will be described with reference to FIGS. 13 to 16.

Figure 13:
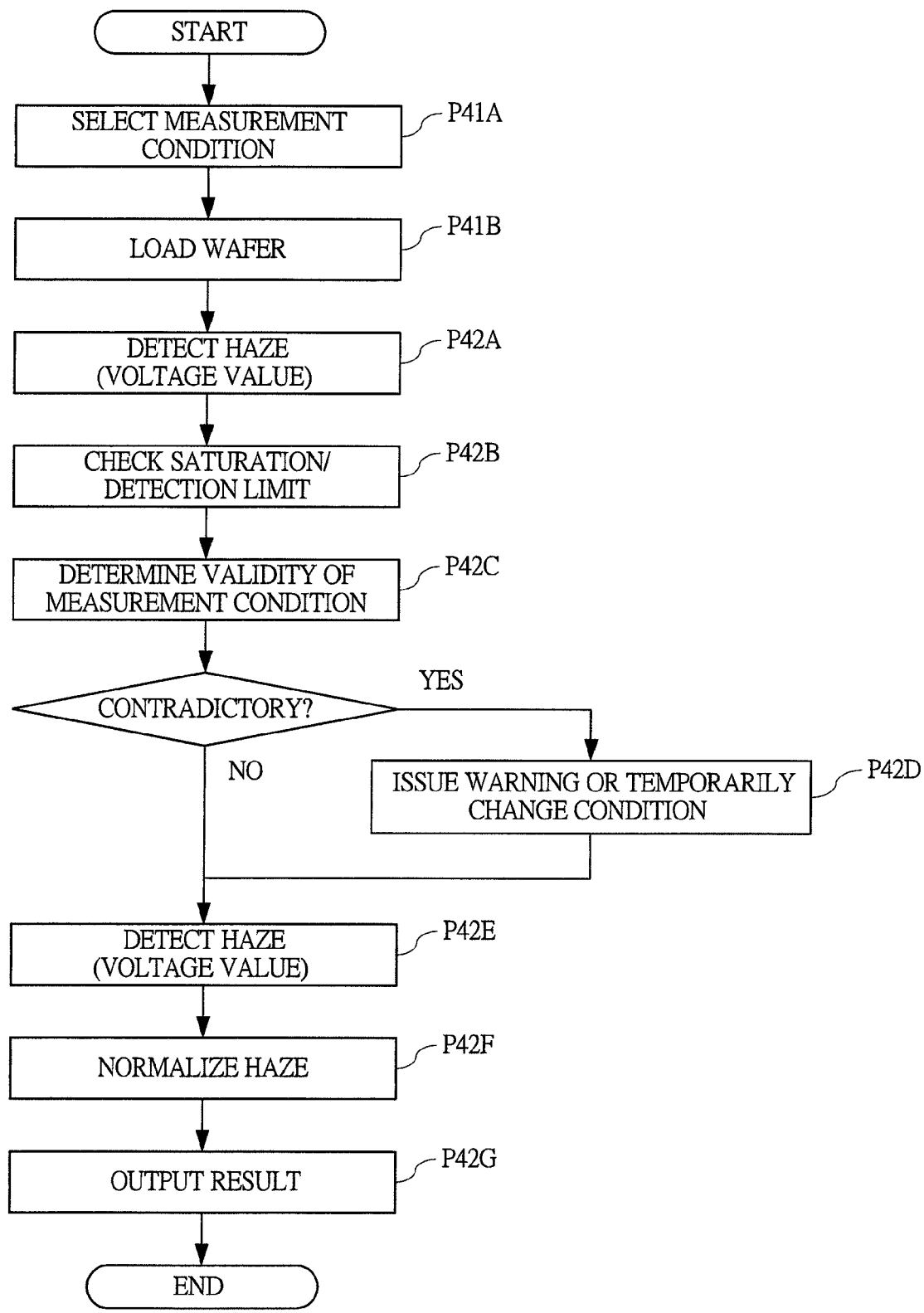
FIG. 13 is a flowchart describing a wafer-surface inspecting process according to an embodiment of the present invention.

FIG. 13 is a flowchart for describing a wafer-surface inspecting process according to the present embodiment.

First, once selection of measurement conditions is performed, such as selection of a wafer to be inspected, selection of a haze area, and an intensity of the luminous light 12 and a range in which an intensity of the scattered light 17 can be measured by the detectors 16A to 16D (process P41A), a wafer corresponding to the selected measurement conditions is loaded to the dark-field inspection apparatus (process P41B).

Next, by detecting the scattered light 17 with the detectors 16A to 16D, detected voltage values in that target area are extracted (process P42A).

Figure 14:
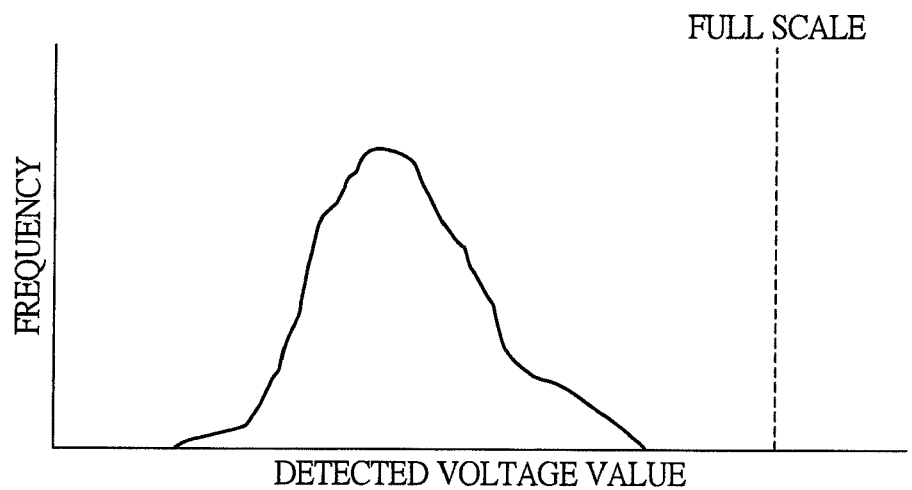
FIG. 14 is an explanatory diagram illustrating an ideal form of frequency of detected voltage values of the dark-field inspection apparatus in the wafer-surface inspecting process according to the embodiment of the present invention.
Figure 15:
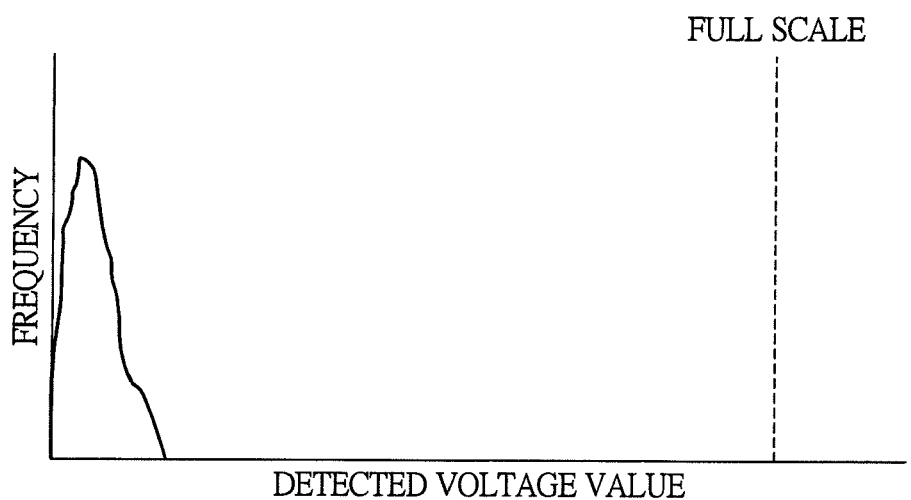
FIG. 15 is an explanatory diagram illustrating a detection limit of frequency of detected voltage values of the dark-field inspection apparatus in the wafer-surface inspecting process according to the embodiment of the present invention.

Here, it is confirmed whether a detection limit or saturation occurs in a histogram of the detected voltage values (whether the values are within a detectable range of the dark-field inspection apparatus) (process P42B), and validity of the measurement conditions selected in the process P41A is determined (process P42C). FIG. 14 is a histogram when the detected voltage values are within a detectable range of the dark-field inspection apparatus, FIG. 15 is a histogram when the detected voltage values are at a detection limit of the dark-field inspection apparatus, and FIG. 16 illustrates a histogram when the detected voltage values are saturated. In the present embodiment, the detection limit exemplarily indicates that the detected voltage values lower than or equal to about 3% of a full scale exceed about 50% of the whole, and saturation exemplarily indicates that the detected voltage values lower than or equal to about 97% of the full scale exceed about 50% of the whole. However, the settings of these 3% and 97% are numerical values to be determined depending on a minimum detection resolving power of the dark-field inspection apparatus, and therefore can be changed as appropriate. As a result of determination, when there is a contradiction among the measurement conditions, a warning is issued to automatically change the measurement conditions so as to prevent occurrence of the detection limit or saturation (process P42D). Here, examples of measurement conditions to be changed include gains of the detectors 16A to 16D, intensity and amplification gain of the luminous light 12, and others. The gains of the detectors 16A to 16D are changed to a ratio to the power of 7.2 between the output voltage value and an applied voltage value. The detected voltage values detected by the detectors 16A to 16D are proportional to the intensity of the luminous light 12, that is, a laser output and an amplifier gain.

Then, the target area set on the surface of the reference wafer is again scanned with the luminous light 12, and the scattered light 17 is detected by the detectors 16A to 16D, thereby extracting the detected voltage values in that target area (process P42E), converting the detected voltage values to actually-measured haze values by normalizing the detected voltage values (process P42F), and outputting the results (process P42G). FIG. 17 is an explanatory diagram illustrating an example of the output actually-measured haze values, the drawing being colored corresponding to the actually-measured haze values. Note that the actually-measured haze values illustrated in FIG. 17 are RMS values, for example.

Note that although RMS values have been used in the present embodiment, Ra values, Rmax values, or Rz values may be used other than RMS values. In this manner, by setting the actually-measured haze values in a format of roughness well known to the operator, such as RMS values or Ra values (a unit standardized in industry, such as JIS), the operator can intuitively know the state of haze.

Also, information about how much certain actually-measured haze values are present on the wafer surface may be represented as a relative value, such as %, or may be represented by using an AD value.

While the invention made by the inventors of the present invention has been concretely described based on the embodiments in the foregoing, it is needless to say that the present invention is not limited to the foregoing embodiments and various modifications and alterations can be made within the scope of the present invention.

In the embodiments described in the foregoing, although a bulk wafer of single crystal silicon has been exemplarily described as a bulk wafer having its surface to be inspected by a dark-field inspecting apparatus, another wafer can be used as long as a thin film layer, such as an epitaxial layer, is not formed on its surface. For example, an SOI (Silicon On Insulator) wafer formed by laminating two single crystal silicon wafers together via a silicon oxide layer may be used.

INDUSTRIAL APPLICABILITY

The reference wafer for calibration of dark-field inspection apparatuses, the method of manufacturing a reference wafer for calibration of dark-field inspection apparatuses, the method of calibrating a dark-field inspection apparatus, the dark-field inspection apparatus, and the wafer inspection apparatus of the present invention can be used in calibration of a dark-field inspection apparatus that inspects the presence or absence of a foreign substance or a roughness degree of a surface of a bulk wafer to be inspected by measuring haze, a reference wafer for calibration of dark-field inspection apparatuses for use in that calibration, a process of manufacturing the reference wafer for calibration of dark-field inspection apparatuses, a dark-field inspection apparatus, and a process of inspecting the surface of a wafer by using the dark-field inspection apparatus.

For example, the number of detectors may be different from that in the dark-field inspection apparatus in the embodiments described above, and a dark-field inspection apparatus may be of a type, such as a type of collecting scattered light using an integrating sphere.

The invention claimed is:

1. An inspection apparatus comprising:
a detection system which detects light from a sample; and
a processing system configured to execute a sequence of programmed instructions which, when executed by the processing system, cause the processing system to perform the following
performing a Fourier transform of roughness of a sample acquired by an atomic force microscopy;
converting a result of the Fourier transform into a spatial frequency function;
converting said roughness into a first signal corresponding to a detection signal of the detection system using the spatial frequency function; and
calibrating the detection system by comparing the first signal to a second signal received from the detection system,
wherein said roughness is substantially free of asperities of an anomaly of said sample.

2. The inspection apparatus according to claim 1,
wherein the processing system determines whether a difference between the first signal and the second signal is in a predetermined range or not.

3. The inspection apparatus according to claim 2,
wherein the calibrating includes changing an output voltage of the detection system.

4. The inspection apparatus according to claim 3,
wherein the calibrating includes changing a gain of the output voltage.

5. The inspection apparatus according to claim 4,
wherein the calibrating includes changing an offset of the output voltage.

6. The inspection apparatus according to claim 5,
wherein the first signal is a first haze signal, and the second signal is a second haze signal.

7. The inspection apparatus according to claim 1,
wherein the calibrating includes changing an output voltage of the detection system.

8. The inspection apparatus according to claim 1,
wherein the calibrating includes changing a gain of an output voltage of the detection system.

9. The inspection apparatus according to claim 1,
wherein the calibrating includes changing an offset of an output voltage of the detection system.

10. The inspection apparatus according to claim 1,
wherein the first signal is a first haze signal, and the second signal is a second haze signal.

11. A system for calibrating an inspection apparatus comprising:
a detection system which detects light from a sample; and
a processing system configured to execute a sequence of programmed instructions which, when executed by the processing system, cause the processing system to perform the following
performing a Fourier transform of roughness of a sample acquired by an atomic force microscopy;
converting a result of the Fourier transform into a spatial frequency function;
converting said roughness into a first signal corresponding to a detection signal of the detection system using the spatial frequency function; and
calibrating the detection system by comparing the first signal to a second signal received from the detection system,
wherein said roughness is substantially free of asperities of an anomaly of said sample.

12. The system according to claim 11,
wherein the processing system determines whether a difference between the first signal and the second signal is in a predetermined range or not.

13. The system according to claim 12,
wherein the calibrating includes changing an output voltage of the detection system.

14. The system according to claim 13,
wherein the calibrating includes changing a gain of the output voltage.

15. The system according to claim 14,
wherein the calibrating includes changing an offset of the output voltage.

16. The system according to claim 15,
wherein the first signal is a first haze signal, and the second signal is a second haze signal.

17. The system according to claim 11,
wherein the calibrating includes changing an output voltage of the detection system.

18. The system according to claim 11,
wherein the calibrating includes changing a gain of an output voltage of the detection system.

19. The system according to claim 11,
wherein the calibrating includes changing an offset of an output voltage of the detection system.

20. The system according to claim 11,
wherein the first signal is a first haze signal, and the second signal is a second haze signal.

21. A method for calibrating an inspection apparatus comprising:
detecting light from a sample using a detection system;
performing, using a processing system, a Fourier transform of roughness of a sample acquired by an atomic force microscopy;
converting, using the processing system, a result of the Fourier transform into a spatial frequency function;
converting, using the processing system, said roughness into a first signal corresponding to a detection signal of the detection system using the spatial frequency function; and
calibrating, using the processing system, the detection system by comparing the first signal to a second signal received from the detection system,
wherein said roughness is substantially free of asperities of an anomaly of said sample.

22. The method according to claim 21,
further comprising determining, using the processing system, whether a difference between the first signal and the second signal is in a predetermined range or not.

23. The method according to claim 22,
wherein the calibrating includes changing an output voltage of the detection system.

24. The method according to claim 23,
wherein the calibrating includes changing a gain of the output voltage.

25. The method according to claim 24,
wherein the calibrating includes changing an offset of the output voltage.

26. The method according to claim 25,
wherein the first signal is a first haze signal, and the second signal is a second haze signal.

27. The method according to claim 21,
wherein the calibrating includes changing an output voltage of the detection system.

28. The method according to claim 21,
wherein the calibrating includes changing a gain of an output voltage of the detection system.

29. The method according to claim 21,
wherein the calibrating includes changing an offset of an output voltage of the detection system.

30. The method according to claim 21,
wherein the first signal is a first haze signal, and the second signal is a second haze signal.

\* \* \* \* \*